United States Patent [19]

Baker

[11] 4,269,059
[45] May 26, 1981

[54] DOSIMETER HAVING CONSTANT FLOW PUMP

[75] Inventor: William B. Baker, Newark, Del.

[73] Assignee: E. I. Du Pont de Nemours and Company, Wilmington, Del.

[21] Appl. No.: 21,810

[22] Filed: Mar. 19, 1979

[51] Int. Cl.³ ............................................. G01N 1/24
[52] U.S. Cl. ...................................................... 73/28
[58] Field of Search ...................... 73/28, 23, 421.5 R, 73/421.5 A; 417/43, 44, 45, 63, 12

[56] References Cited

U.S. PATENT DOCUMENTS

| | | |
|---|---|---|
| 1,910,202 | 5/1933 | Crago . |
| 2,889,780 | 6/1959 | Binford . |
| 2,982,131 | 5/1961 | Rosinski . |
| 3,129,587 | 4/1964 | Hallanger . |
| 3,198,121 | 8/1965 | Schaub . |
| 3,269,320 | 8/1966 | Tilley et al. . |
| 3,410,059 | 11/1968 | Garnier ..................... 73/28 |
| 3,411,704 | 11/1968 | Hilgert et al. . |
| 3,424,370 | 1/1969 | Law . |
| 3,501,899 | 3/1970 | Allen ...................... 417/43 |
| 3,537,296 | 11/1970 | Gamache ................. 73/23 |
| 3,701,280 | 10/1972 | Stroman ................. 73/23 |
| 3,726,607 | 4/1973 | Garman ................. 417/43 |
| 3,748,906 | 7/1973 | Manka ............. 73/421.5 A |
| 3,784,902 | 1/1974 | Huber ...................... 73/28 |
| 3,814,544 | 6/1974 | Roberts et al. .......... 417/40 |
| 3,865,512 | 2/1975 | Deters ..................... 417/44 |
| 3,882,861 | 5/1975 | Kettering et al. ....... 417/44 |
| 3,949,734 | 4/1976 | Edwards et al. ........ 417/43 |
| 3,953,152 | 4/1976 | Sipin ....................... 73/28 |
| 3,956,940 | 5/1976 | Guild ...................... 73/28 |
| 3,989,913 | 11/1976 | Lundquist et al. ...... 417/12 |
| 4,063,824 | 12/1977 | Baker et al. ............ 417/43 |
| 4,123,932 | 11/1978 | Baker et al. ............ 73/28 |

Primary Examiner—Stephen A. Kreitman

[57] ABSTRACT

An improved dosimeter designed for individual use that has a filter for collecting particles or vapors present in an air stream being pumped through the dosimeter, a variable drive pump that draws the air stream through the filter, an electric motor coupled to the variable drive pump, an electric power source for the motor, an air reservoir connected to the pump, an orifice position in a tube attached to the air reservoir which creates a pressure drop in the air stream, a differential pressure switch positioned before the orifice that is activated by a change in air pressure and creates a low voltage electrical input signal; an integrator circuit that uses the low voltage input signal of the pressure switch and integrates this signal, an amplifier circuit which amplifies the signal from the integrator circuit and feeds the signal to the electric motor thereby controlling the speed of the motor driving the pump in relationship to the signal generated by the pressure switch to maintain the air stream at a constant flow rate; the improvement that is used therewith is as follows:

an accumulator positioned before the variable drive pump retains air and maintains an even flow of air of the inlet of the pump and a pulsation air pressure filter assembly positioned between the orifice and the pressure switch reduces pulsations in the air stream thereby limiting the activity of the switch to substantial changes in air pressure of the air stream.

10 Claims, 2 Drawing Figures

DOSIMETER HAVING CONSTANT FLOW PUMP

BACKGROUND OF THE INVENTION

Field Of The Invention

This invention relates to a dosimeter and in particular to a dosimeter designed for individual use that has a constant air stream flowing through the dosimeter.

Dosimeters are known and have been used by individuals in an effort to determine the level of exposure of an individual to foreign substances in air, for example, to vapors or fumes, dust particles and the like. The dosimeter is worn by the individual and air is pumped through a filter which traps foreign substances in the air. At the end of an individual's exposure period, the filter is removed and analyzed for any foreign substances. The problem has been with these dosimeters that the air flow rate through the dosimeter has not been accurately controlled. For example, if the filter was partially blocked so that intake of air was momentarily stopped or reduced for a period of time, it was not possible to adjust and increase the flow rate of air to compensate for the stoppage or reduction of air passing through the filter of the dosimeter. Any reduction in the air flow rate reduces the amount of foreign substances collected by the filter thereby giving an inaccurate level of exposure of the individual.

The aforementioned problem has been substantially solved with the dosimeter described in Baker et al. U.S. Pat. No. 4,063,824 issued Dec. 20, 1977. However, dosimeters requiring an air flow rate of about 1–3 liters per minute present special problems and require additional control of the air being pumped through the dosimeter to provide a uniform smooth air flow rate.

SUMMARY OF THE INVENTION

An improved dosimeter designed for individual use that has an intake port connected to a filter means in which particles or vapors present in an air stream being pumped through the dosimeter are collected on the filter means, a variable drive pump is connected to the filter means and draws the air stream through the filter means and pumps the air stream through the dosimeter, an electric motor is coupled to the variable drive pump and operates the pump, an electric power source is coupled to the electric motor, an air reservoir connected to the pump retains any excess air supplied by the pump to maintain a constant flow rate of the air stream, an orifice position in a tube attached to the air reservoir whereby a pressure drop is created when the air stream is pumped through the orifice, a differential pressure switch positioned before the orifice that is activated by a change in air pressure of the air stream and creates a low voltage electrical input;

an integrator circuit electrically connected to the power source and to the pressure switch uses the low voltage input signal of the pressure switch and integrates this signal, an amplifier circuit electrically connected to the power source and the integrator circuit which amplifies the signal from the integrator circuit and feeds the amplified signal to the electric motor thereby controlling the speed of the motor driving the pump in relationship to the signal generated by the pressure switch to maintain the air stream at a constant flow rate; the improvement that is used therewith comprises:

an accumulator positioned between the intake part and the variable drive pump which retains air and maintains an even flow of air to the inlet of the pump and a pulsation air pressure filter assembly positioned between the orifice and the pressure switch which reduces pulsations in the air stream in contact with the pressure switch thereby limiting the activity of the pressure switch only to substantial changes in air pressure of the air stream.

DETAILED DESCRIPTION OF THE INVENTION

The dosimeter which contains an accumulator and a pulsation air pressure filter assembly provides a uniform smooth flow of the air stream through the dosimeter at an air flow rate of 1–3 liters per minute. The dosimeter is of a relatively low cost construction and does not use an additional pump or high cost control apparatus to achieve this uniform air flow rate.

The dosimeter is designed primarily for individual use and is compact in size and is about 4 cm × 10 cm × 16 cm and weighs about 723 g. The dosimeter can be carried by a worker, for example, in a pocket, or a belt, in a neck band and the like, without inconvenience or hindrance to work activities. The dosimeter is rugged in design and is useful for service in industrial environments.

The dosimeter with its constant flow feature improves the accuracy with which a wide variety of environmental hazards to individuals can be monitored. Monitoring for dust in mines or mills vinyl chloride or benzene vapors in industrial work areas and toxic radon gas and toxic related products of radon gas in mines are typical of important applications of the dosimeter.

Figure 1:
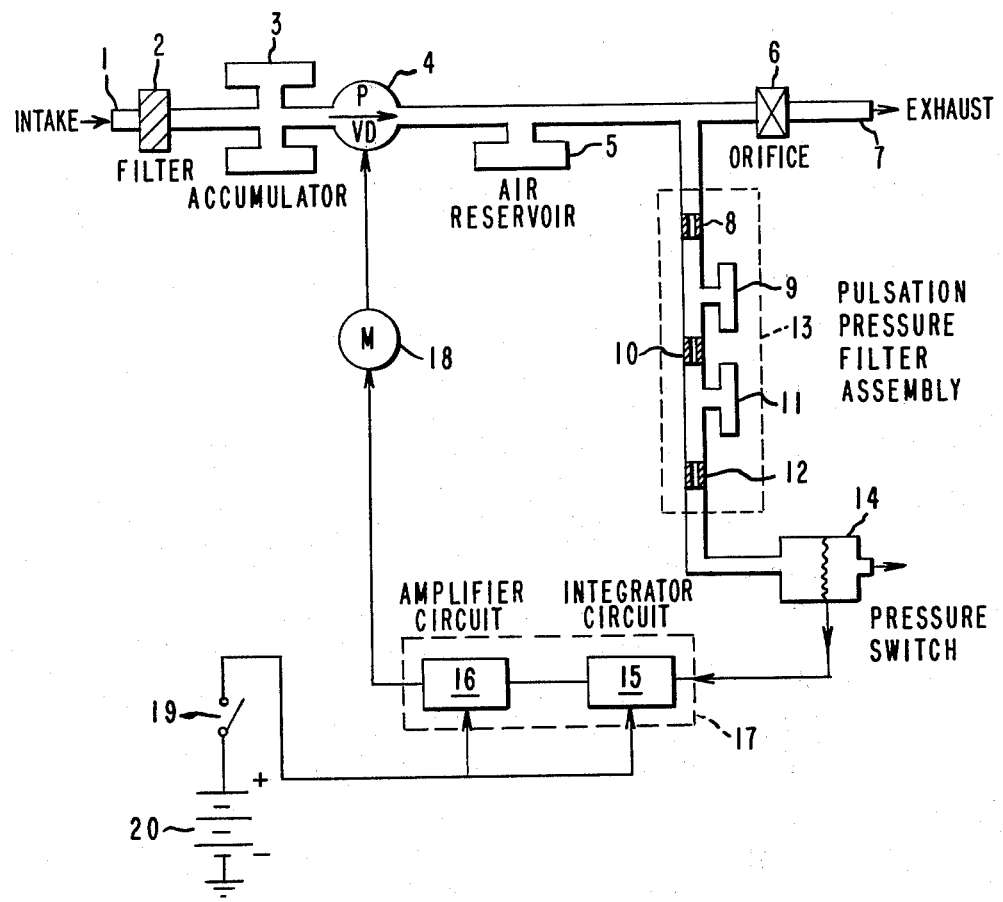
FIG. 1 is a block diagram of the dosimeter.

Referring to the block diagram of FIG. 1, a basic arrangement of the dosimeter is shown. Air is pumped in at the intake 1 at a constant flow rate and passed through a collector or filter 2. The air intake and collector or filter are tubularly connected to an accumulator 3 which is connected by a passage to a variable drive pump 4 driven by an electric D.C. motor 18.

The accumulator allows for a buildup of excess air on the suction side of the variable pump and helps to moderate the flow of air by reducing surges of air created by strokes of the pump. From the pump 4, air is pumped to the air reservoir 5 which also moderates the flow of air and reduces surges of air created by the pump. An orifice 6 such as an adjustable needle valve is positioned in a passage leading to the exhaust port 7 and causes an air pressure drop. A pressure switch 14 is positioned before the orifice and is activated by any change in the air pressure drop. To reduce surges in the air, a pulsation filter assembly 13 is positioned in a passage before the pressure switch. One side of the pressure switch is exposed to the air stream while the other side is open to the atmosphere. When the pressure switch 14 is activated by a change in the air pressure drop, an electrical signal is generated and this signal is fed to the integrator circuit 15 that is electrically connected to the pressure switch. The integrator circuit integrates this signal which is then fed to the amplifier circuit 16 which amplifies the signal. Both the integrator circuit and the amplifier circuit can be formed on an electronic chip 17.

The amplified signal controls the speed of the electric motor 18 driving the air pump 4 and thereby provides a constant flow of air through the dosimeter. The integrator and amplifier circuits are electrically connected to a D.C. power source 20 which usually is a battery. An on-off switch 19 is positioned between the power source 20 and the amplifier and integrator circuits.

Configurations other than the above for the dosimeter can be used. The dosimeter can be used to fill bags with air samples by attaching a bag to the exhaust port. To accomplish this, the low pressure side of the pressure switch 14 is connected to the exhaust port 7 through another pulsation pressure filter identical to 13. Optionally, the two pulsation pressure filter assembles could be combined to form a differential pulsation pressure filter.

If a filter such as a charcoal filter is used that is not sensitive to pulsations in the air stream, it is possible to remove the accumulator 3. If a multicylinder pump, such as a four cylinder pump which only causes small pulsations, it may be possible to eliminate the accumulator 3 and/or the air reservoir 5.

The orifice 6, the pulsation pressure filter assembly 13 and pressure switch 14 can be positioned between the filter 2 and the accumulator 3. With this configuration, the air reservoir 5 can be eliminated. However, a differential connection of the filter would be required and the pulsation pressure assembly and pressure switch would be exposed to an inlet air pressure drop across the filter and would be prone to air leaks.

The filter or collector 2 of the dosimeter can be adapted to entrap almost any type of substance such as gases, liquids or solids. If mechanical filtration is only required, for example, to collect dust particles to which a worker is exposed, a filter is provided which will entrap particles of 0.01 microns or larger. If the filter is to entrap a gas such as sulfur dioxide, a chemical filter is used which will entrap this gas or the air stream can be bubbled through a solution which reacts with this gas. If vapors are to be entrapped, then a filter such as a charcoal filter, is used which entraps vapors. A clean filter or collector is placed in the dosimeter at the start of a work period, such as an eight hour shift. At the end of the period, the filter is removed and examined for the substance or substances to which the individual was exposed. A simple count of particles under a microscope may be used or the filter can be analyzed, for example, with a gas chromatograph.

The accumulator 3 is usually an integral part of any frame on which various components used in the dosimeter are enclosed or mounted on and is milled or cut into the frame with appropriate openings. Preferably, at least one wall of the accumulator is a thin flexible material such as "Neoprene" rubber. A typical accumulator has a volume of about 5–20 cc. As pointed above, the purpose of the accumulator is to reduce or moderate surges of air created by strokes of the pump by allowing a build-up of air on the suction side of the pump.

A variable drive air pump is used in the dosimeter. Generally, a diaphragm type pump is used that pumps from about 1 to 3 liters per minute. Other pumps such as piston pumps, rotary pumps and centrifugal pumps can also be used. Preferably a diaphragm pump is used in which the valves are of an elastomeric material or a plastic such as polyester like polyethylene terephthalate.

The pump is electrically connected to a conventional D.C. motor of about 0.0001–0.02 horsepower. The motor is a variable speed motor and operates from about 1,000 to 20,000 revolutions per minute. Under some circumstances, a reducing gear can be used between the motor and the pump.

The air reservoir is usually an integral part of the frame on which the various components used in the dosimeter are mounted and is milled or cut into the framework with appropriate openings. Part of the reservoir may be enclosed with a thin sheet of an elastomer so that any pulsations of the air stream created by the pump can be readily dampened by the elastomer absorbing the pulsation.

The purpose of the reservoir is to smooth pulsations of the air stream created by the strokes of the pump at least to some degree before the air stream passes through the orifice. The volume of the reservoir is as small as possible but of sufficient volume to reduce the pulsations of the air stream. A typical reservoir has a volume of about 1–5 cc.

An orifice such as an adjustable needle valve is positioned in a tube connecting the reservoir to the exhaust port. An orifice is used that creates a pressure drop of about 0.4–4.0 inches (1–10 cm) of water. Usually a pressure drop of 2.5–3.5 inches (6.35–8.25 cm) of water is used.

A pulsation pressure filter assembly 13 is positioned in the air stream before the orifice 6 and before the pressure switch 14 which is in parallel to the orifice. The assembly substantially reduces and often eliminates pulsations and surges of air caused by the pump so that the pressure switch does not operate on each pressure surge created by each pump stroke and thereby substantially extends the life of the pressure switch. The pulsation filter also causes a delay of the pressure signal traveling to the pressure switch. This delay causes the circuitry controlling the pump to increase the speed or slow the speed of the pump in a repeatable manner.

The elements of the pulsation pressure filter assembly 13 are shown in FIG. 1. The air from the pump flows through the orifice 6 and a pressure drop across the orifice is created which generates a higher pressure on the inlet than on the exhaust side of the orifice. The higher pressure is transmitted to the pressure switch through orifices 8, 10 and 12. A pressure surge in the air stream on the inlet of the orifice 6, first passes through orifice 8 and fills the chamber of the accumulator 9. The surge then passes through orifice 10 and then into the chamber of accumulator 11 and then through orifice 12 to the pressure switch 14. The opposite side of the pressure switch is open to the atmosphere. Thus the pulsation filter moderates the air pressure surges in the air stream and provides a relatively constant level of pressure to the pressure switch which represents the average of the pressure drop generated across orifice 6 and allows for smooth and continuous operation of the air pump since the signal generated by the pressure switch is utilized by the integrator circuit to control the operation of the air pump.

Generally, a pressure switch is used that has a set point that is about the same as the pressure drop across the orifice and that is sensitive to a pressure drop change in the air stream of about 0.01–0.5 inches (0.0254–1.27 cm) of water. The sensitivity of the switch or the amount of pressure required to activate the switch determines the number of signal changes fed to the integrator. A switch having a low level of sensitivity would feed fewer on-off changes of signal to the integrator than would a switch of high sensitivity. A switch with a fixed level of sensitivity or a switch with an adjustable level of sensitivity can be used.

The flow rate of the air stream is determined by the size opening in the orifice and by the sensitivity of the pressure switch. When it is desired to operate under fixed conditions, a non-adjustable orifice can be used with a fixed pressure switch. When it is desired to operate under variable conditions, an adjustable orifice or an adjustable pressure switch can be used or both the orifice and the pressure switch can be adjustable.

The integrator circuit takes the on-off signal generated by the pressure switch and formulates a slowly changing continuous signal therefrom which is fed into the amplifier circuit. The integrator circuit is biased at about +0.6 volts and the signal from the switch increases to about 1.2 volts when the pressure switch is activated and decreases to about +0.0 volts when the switch is deactivated. The integrator circuit produces a gradually decreasing output voltage which feeds into the amplifier when the pressure switch is closed and a gradually increasing voltage when the pressure switch is open. The circuit is constructed of conventional transistors, capacitors and resistors.

The amplifier circuit receives the signal generated by the integrator circuit and amplifies the signal so that the electric D.C. motor can be controlled at various speeds to insure a constant flow rate of the air stream through the dosimeter. The amplifier circuit amplifies the signal from the integrator to a maximum of about 95% of the total voltage of the power source. For example, for a 5 volt power source, the signal will be amplified to 4.8 volts. Generally, the amplifier has an impedance of greater than 10 ohms and up to 1 megohm. However, an amplifier with an impedance of less than 10 ohms can be used, e.g., 0.01–10 ohms impedance. The amplifier is constructed of conventional transistors, capacitors and resistors.

The power-source usually is a battery of about 5–6 volts. Generally, a nickel cadmium battery of 4 cells is used. A direct current power source of rectified A.C. current can also be used.

One optional circuit that can be used in the dosimeter is a battery check circuit. The circuit uses a precision voltage detector which can be adjusted to the voltage of each cell and is set to be activated at the full charge voltage of the battery. A light emitting diode which is activated by a switch is usually used to indicate a full charge of the battery.

Another optional circuit that can be used in the dosimeter is a low air flow detector circuit which is connected to the integrator circuit and is activated when the voltage output of the integrator circuit is at higher than normal operational levels caused by an interruption of the air stream being pumped through the dosimeter. The low flow detector circuit comprises a bistable multivibrator circuit electrically connected to an indicator light such as a light emitting diode.

Useful integrator circuits, amplifier circuits, low flow air detector circuits and battery check circuits are disclosed in Baker et al. U.S. Pat. No. 4,063,824 issued Dec. 20, 1977 and Baker et al U.S. Pat. No. 4,123,932 issued Nov. 7, 1978. The applicable portions of these patents are hereby incorporated by reference. These circuits can be formed in an integrated circuit chip. The chip is preferred because of its small size and simple installation and replacement.

Figure 2:
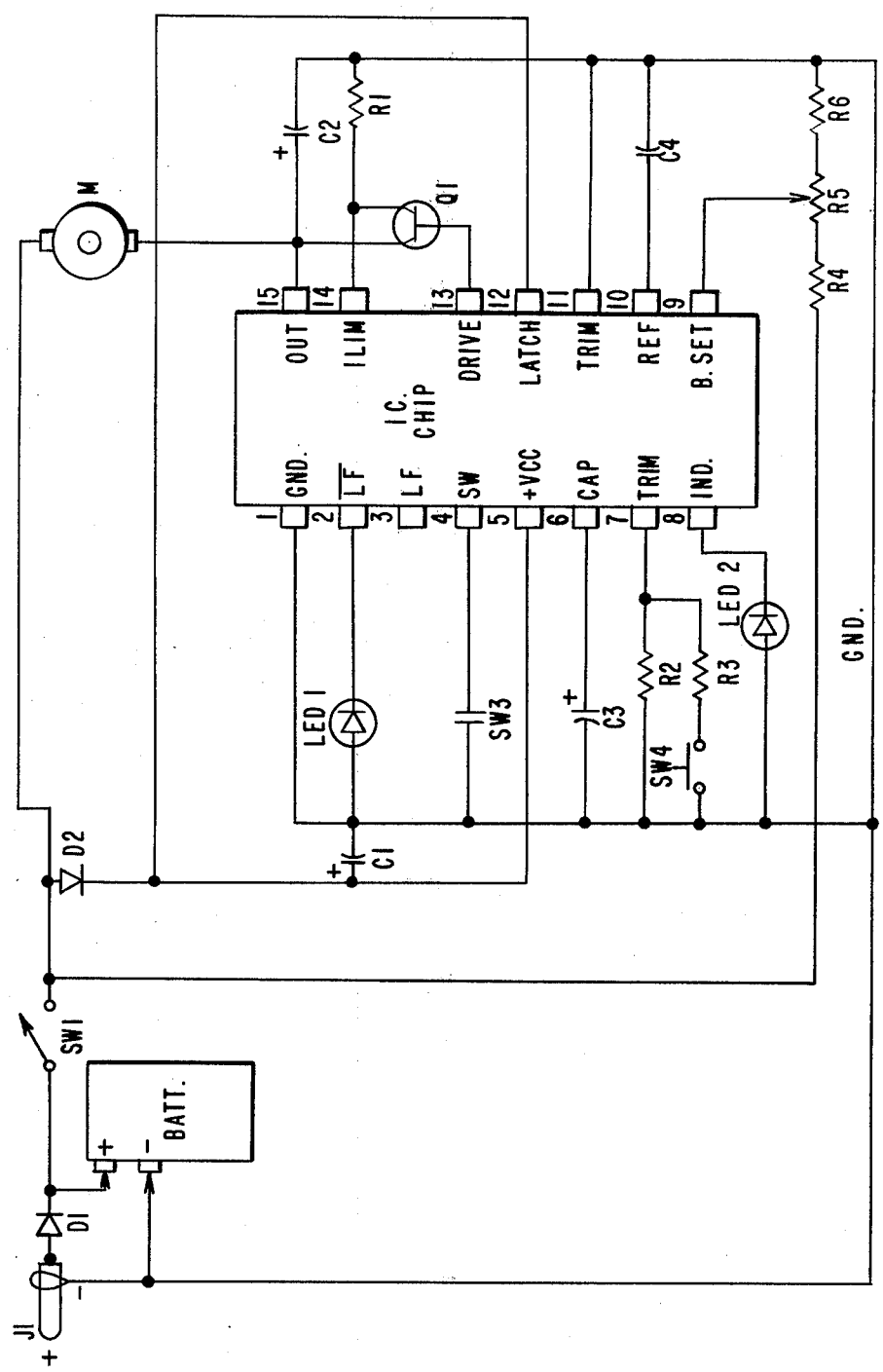
FIG. 2 is a schematic circuit diagram for one embodiment of the dosimeter.

FIG. 2 shows a schematic circuit diagram of the circuit used in the dosimeter.

The circuit is based on an integrated circuit chip (IC Chip). The chip contains an integrator circuit, amplifier circuit, battery check circuit and low flow detector circuit. The internal construction of the chip is made of conventional transistor circuits and is made according to conventional techniques well known to those skilled in the art of making integrated circuit chips. The chip has fifteen terminals which connect to external functional electrical components of the circuit.

To power the motor (M) connected to the pump, switch SW1 is placed in the ON position and feeds power from the battery (BATT) to the Motor (M) and via diode D2 (typically IN4001) to the chip circuit via power input terminal 5 (+VCC). Diode D2 prevents circuit damage if the battery is accidentally connected with the polarity reversed.

Capacitor C1 (typically 2.2. microfarads) connected between terminal 5 and ground filters out electrical noise. In the operation of the integrator circuit of the chip, the voltage across capacitor C3 (typically 10 microfarad) connected to terminal #6 (CAP) is always either increasing or decreasing depending on the state of pressure switch SW 3. When the air flow rate is low, SW3 is open and the voltage at terminal #6 increases and when the air flow rate is high, SW3 is closed which connects terminal #4 (SW) to terminal #1 (GND) which is the COMMON terminal for the chip and the voltage decreases. The rate of increase and decrease of voltage (time constant) is determined by capacitor C3 and resistor R2 (typically 2.2 megohms). R2 is connected to ground (G.N.D.) and terminal 7 (TRIM) connected to the integrator circuit of the chip.

To provide a shorter time constant when first starting the pump, momentary switch SW2 is closed connecting R3 (typically 100 K ohms) in parallel to R2. SW2 connected to ground and to R3. R2 is connected to terminal 7 of the chip.

In the chip the voltage from the integrator circuit is fed to the amplifier circuit. The amplifier circuit is connected to terminal 13 (DRIVE), terminal 14 (ILIM) and terminal 15 (OUT). The output transistor Q1 (typically D40-D2) is connected to terminals 13, 14 and 15 and provides additional voltage to the motor.

Resistor R1 (typically 1 ohm) connected between terminal 15 and ground sets the maximum current value that the amplifier circuit will produce. Capacitor C2 (typically 2.2 microfarads) connected between terminal 15 and ground stabilizes the amplifier voltage output.

In the chip, the voltage from the integrator circuit is also fed to the low flow detector circuit. A higher than normal voltage from the integrator circuit indicates low air flow through the pump. When this occurs, the low flow detector circuit is triggered and terminal 3 (LF) is energized and terminal 2 (LF) deenergized. Either terminal can be connected to a light emitting diode (LED 1) to give the desired indication of air flow. With LED 1 connected between terminal 2 and ground, the LED indicates proper flow control by remaining on and upon low flow, the LED will extinguish. With the LED connected between terminal 3 and ground, the LED indicates proper flow control by remaining off and when there is a low flow the LED will light.

Under conditions when low air flow occurs and the low flow detector circuit is triggered and subsequently the air flow is corrected to normal flow, terminals 2 and 3 remain latched in their low flow state because of the connection of terminal 12 to terminal 5. Terminals 2 and 3 remain in the latched position until the power is turned off and will keep LED 1 in its lit or unlit state which indicates low flow. Optionally, the connection between terminal 12 and 5 can be omitted, then terminals 2 and 3 would return to their original state when the low flow condition is corrected.

In the chip, the battery check circuit drives the light emitting diode (LED 2) connected terminal 8 (IND) when the battery voltage is above a certain level. Resistors $R^4$ (typically 20 K ohm), $R^5$ (typically 5 K ohm) and $R^6$ (typically 5.1 K ohm) are serially connected between the power switch and ground with the wiper of $R^5$ connected to terminal 9 (B. SET) to provide a percentage of the battery voltage to the battery check circuit. When this voltage is higher than an interval precision reference voltage set in the chip, power is provided to terminal 8 which lights LED 2 indicating that the battery is fully charged. When the above voltage is lower than the interval precision reference voltage, LED 2 is not energized indicating that the battery is not fully charged.

A precision reference voltage is generated in the integrated circuit chip for the battery check circuit. Terminal 11 (TRIM) is normally connected to ground. If necessary a resistor can be connected between terminal 11 and ground to provide better temperature stability.

Capacitor C4 (typically 0.02 microfarads) is connected from terminal 10 (REF) to ground to provide filtering of the precision reference voltage.

The battery can be charged by a nickel cadium battery charger through charging jack J1. Diode D1 (typically IN 4001) is connected from J1 to the positive terminal of the battery to prevent current flow if the jack is accidentally shorted.

In practical operation of the dosimeter a worker is given the dosimeter to wear for an 8 hour shift. At the end of the shift, the LED of the flow control circuit is observed to determine if the intake was blocked during the shift. The filter is then removed from the dosimeter and sent to a laboratory for analysis and the results are recorded in the worker's files. If there is excessive exposure, the worker can be withdrawn from the particular area and given another job.

It is practical to maintain a dosimeter bank from which each worker draws his own dosimeter at the beginning of his work shift and is returned at the end of the shift.

It may be preferred to monitor only one worker of a given group and assume that the entire group has received the same exposure. If desired, individual dosimeters can be statically mounted in specific work areas and individual exposure can be approximated according to the time spent by the worker in a particular area.

I claim:

1. An improved dosimeter that has an intake port connected to a filter means in which particles or vapors present in an air stream being pumped through the dosimeter are collected on the filter means, a variable drive pump is connected to the filter means and draws the air stream through the filter means and pumps the air stream through the dosimeter, an electric motor is coupled to the variable drive pump and operates the pump, an electric power source is coupled to the electric motor, an air reservoir connected to the pump retains any excess air supplied by the pump to maintain a constant flow rate of the air stream, an orifice positioned in a tube attached to the air reservoir whereby a pressure drop is created when the air stream is pumped through the orifice, a differential pressure switch positioned before the orifice that is activated by a change in air pressure of the air stream and creates a low voltage electrical input signal; an integrator circuit electrically connected to the power source and to the pressure switch uses the low voltage input signal of the pressure switch and integrates this signal, an amplifier circuit electrically connected to the power source and the integrator circuit which amplifies the signal from the integrator circuit and feeds the amplified signal to the electric motor thereby controlling the speed of the motor driving the pump in relationship to the signal generated by the pressure switch to maintain the air stream at a constant flow rate; the improvement in use therewith comprises:

an accumulator positioned before and connected to the variable drive pump which retains air and maintains an even flow of air to the inlet of the pump and a pulsation air pressure filter assembly positioned between the orifice and the pressure switch which reduces pulsations in the air stream in contact with the pressure switch thereby limiting the activity of the pressure switch to substantial changes in air pressure of the air stream.

2. The improved dosimeter of claim 1 wherein the pulsation air pressure filter assembly comprises at least one orifice in combination with an air chamber.

3. The improved dosimeter of claim 1 wherein the pulsation air pressure filter assembly comprises an orifice in combination with an air chamber connected to a second orifice in combination with an air chamber connected to a third orifice.

4. The improved dosimeter of claim 2 in which the variable drive pump is a diaphragm pump.

5. The improved dosimeter of claim 4 in which the diaphragm pump has a valve of a flexible polymeric material.

6. The improved dosimeter of claim 5 in which the valve is of a thin polyester film.

7. The improved dosimeter of claim 1 which has electrically connected thereto a low air flow detector circuit comprising a bistable multivibrator circuit electrically connected to an indicator light.

8. The improved dosimeter of claim 1 which has electrically connected thereto a battery check circuit comprising a precision voltage detector adjusted to the voltage of each cell of the battery.

9. The improved dosimeter of claim 1 in which the integrator, amplifier, low air flow detector and battery check circuits are on an electronic chip.

10. The improved dosimeter of claim 1 wherein
the air pressure filter assembly comprises an orifice in combination with an air chamber connected to a second orifice in combination with an air chamber connected to a third orifice;
the variable drive pump is a diaphragm pump having a valve of a thin flexible polyester film;
a low air flow detector circuit electrically connected thereto comprising a bistable multivibrator is electrically connected to a light emitting diode;
a battery check circuit electrically connected thereto comprising a precision voltage detector adjusted to the voltage of each cell of the battery; and the integrator, amplifier, low air flow detector and battery check circuits are on an electronic chip.

* * * * *